US005868244A

United States Patent [19]
Ivanov et al.

[11] Patent Number: 5,868,244
[45] Date of Patent: Feb. 9, 1999

[54] MICROBIAL BARRIER VENTED PACKAGE FOR STERILE MEDICAL DEVICES AND METHOD OF PACKAGING

[75] Inventors: Konstantin Ivanov, Bound Brook; William Reinhardt, Belle Mead; Shakti Routh, Ringos; Michael Pohle, Flemington, all of N.J.

[73] Assignee: Ethicon, Inc., Somerville, N.J.

[21] Appl. No.: 982,055

[22] Filed: Dec. 1, 1997

[51] Int. Cl.⁶ .................................................. A61B 17/06
[52] U.S. Cl. .......................... 206/63.3; 206/439; 53/425; 53/432; 53/433
[58] Field of Search .................................... 206/63.3, 438, 206/439; 53/415, 425, 432, 433

[56] References Cited

U.S. PATENT DOCUMENTS

| | | | |
|---|---|---|---|
| 2,870,954 | 1/1959 | Kulesza | 53/432 |
| 2,917,878 | 12/1959 | Carnarius et al. | 53/22 |
| 3,088,255 | 5/1963 | Griem | 53/425 |
| 3,353,664 | 11/1967 | Carnarius et al. | 206/63.2 |
| 3,716,961 | 2/1973 | Cope et al. . | |
| 3,726,057 | 4/1973 | Kemble . | |
| 3,728,839 | 4/1973 | Glick . | |
| 3,815,315 | 6/1974 | Glick . | |
| 3,926,311 | 12/1975 | Laske . | |
| 4,022,324 | 5/1977 | Schuster | 206/439 |
| 4,270,658 | 6/1981 | Schuster . | |
| 4,482,053 | 11/1984 | Alpern et al. . | |
| 4,588,085 | 5/1986 | Sussman . | |
| 4,603,538 | 8/1986 | Shave . | |
| 4,777,782 | 10/1988 | Nixon, Jr. et al. . | |
| 4,805,377 | 2/1989 | Carter . | |
| 4,831,811 | 5/1989 | Nixon, Jr. et al. . | |
| 4,884,694 | 12/1989 | Sengewald | 206/439 |
| 4,947,620 | 8/1990 | Carter . | |
| 5,203,458 | 4/1993 | Cornwell | 206/438 |
| 5,464,580 | 11/1995 | Popescu et al. . | |
| 5,617,705 | 4/1997 | Sanfilippo et al. | 53/432 |
| 5,623,810 | 4/1997 | Dey et al. . | |
| 5,709,067 | 1/1998 | Dey et al. . | |
| 5,732,529 | 3/1998 | Dey et al. . | |

FOREIGN PATENT DOCUMENTS

| | | | | |
|---|---|---|---|---|
| 1569479 | 6/1980 | United Kingdom | | B65D 81/20 |

Primary Examiner—David T. Fidel
Attorney, Agent, or Firm—Emil Richard Skula

[57] ABSTRACT

A package for sterilized, absorbable medical devices is disclosed. The package has a plurality of cavities in communication with a vent, wherein the vent is preferably centrally located. After sterilization, the package is sealed adjacent to the vent thereby providing individual hermetically sealed sterile cavities which are cut away from the package to form unitary packages.

45 Claims, 18 Drawing Sheets

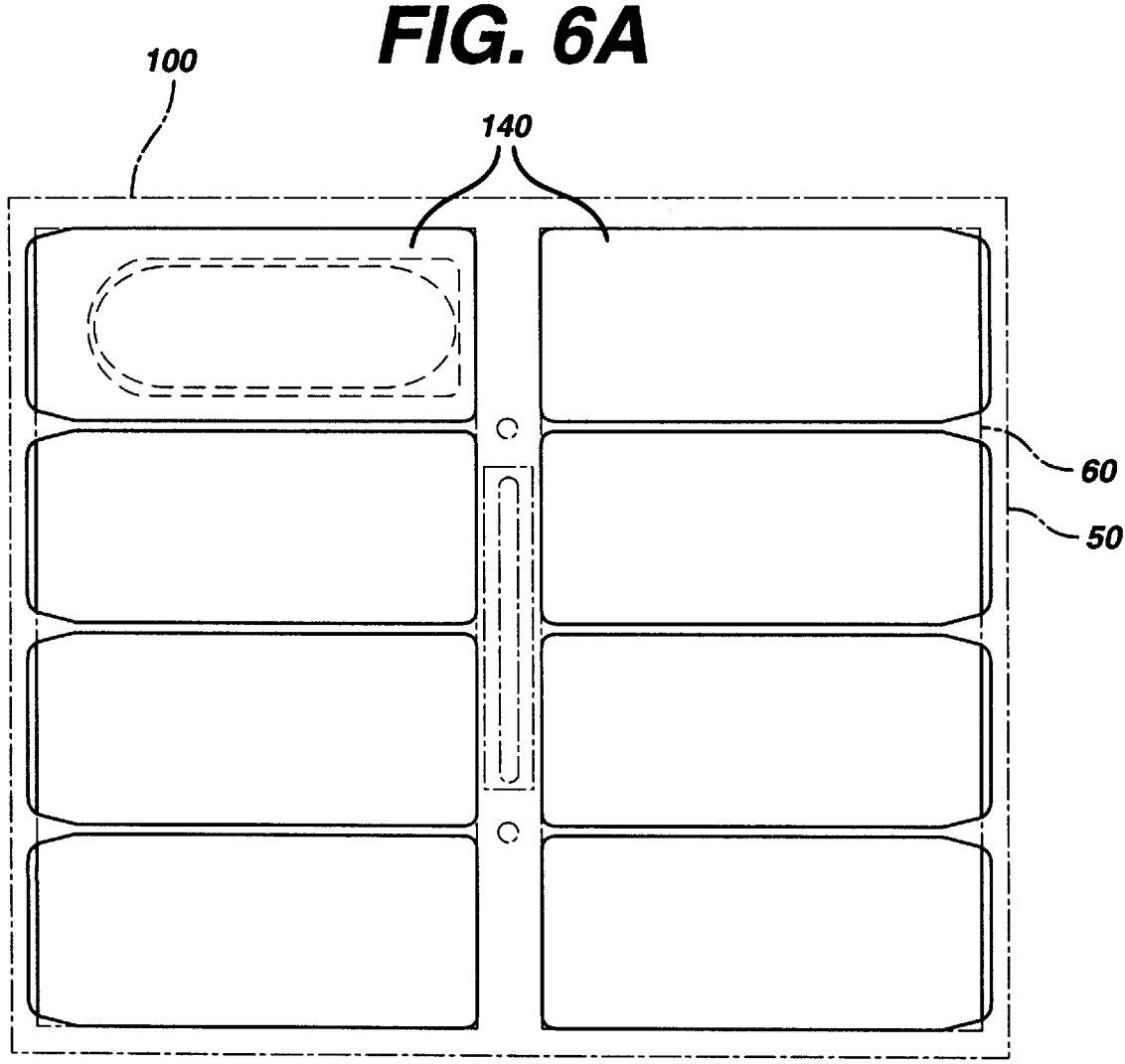

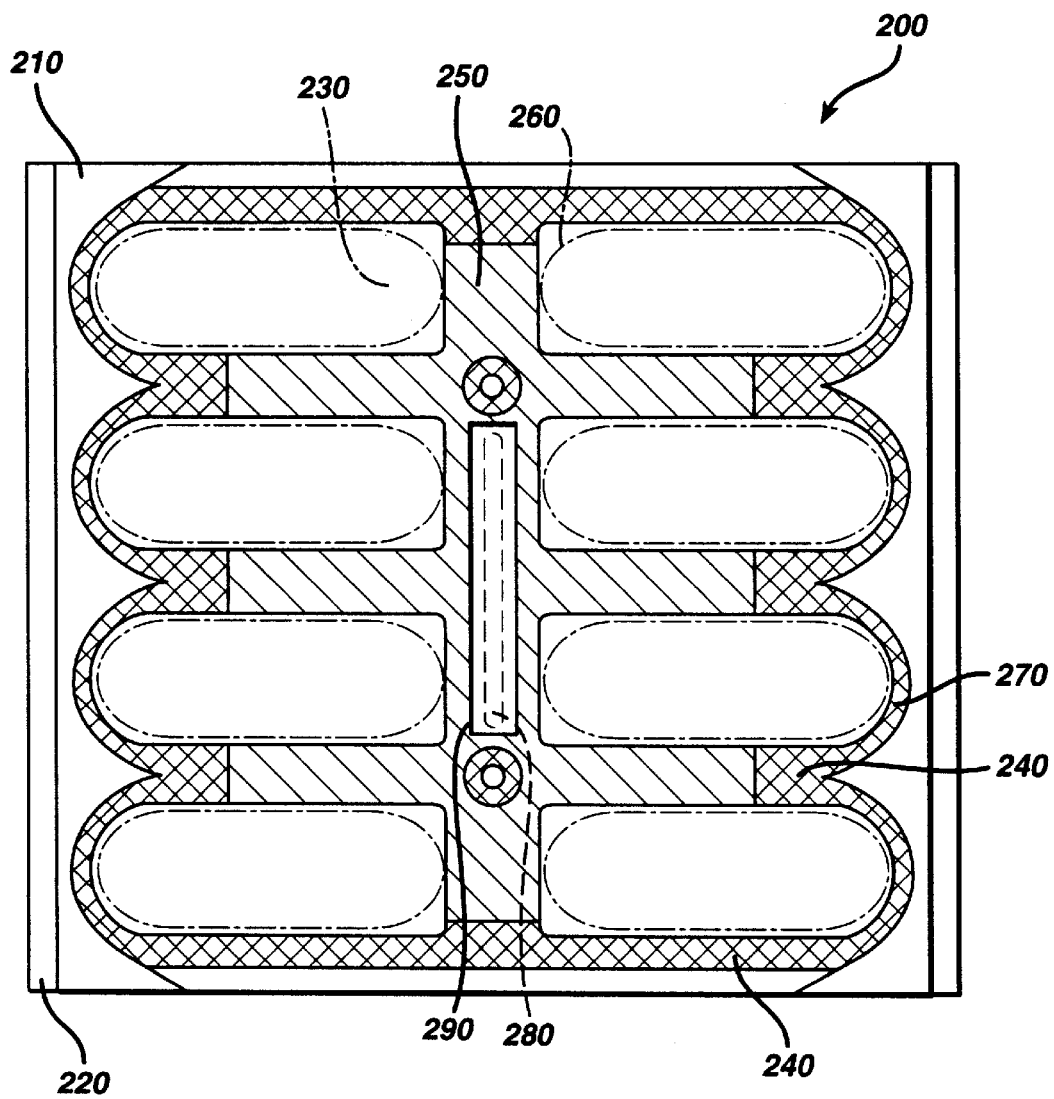

MICROBIAL BARRIER VENTED PACKAGE FOR STERILE MEDICAL DEVICES AND METHOD OF PACKAGING

TECHNICAL FIELD

The field of art to which this invention relates if packaging, in particular, packages for sterile medical devices such as surgical sutures.

BACKGROUND OF THE INVENTION

Packages for medical devices, including surgical needles and sutures are well known in the art. Surgical sutures are typically manufactured with surgical needles mounted to one or both ends of the suture. The surgical needle and suture combinations are typically packaged in a variety of conventional packages. One type of conventional package typically used is a folder package made from a stiff, medical grade paper. A folder package will typically have a plurality of foldable panels and cut-out tabs and tab pockets. In addition, a needle park is typically mounted to one of the panels for receiving and holding one or more surgical needles. In order to package a surgical suture and surgical needle combination in a conventional folder package, the needle is first typically mounted in a needle park, then the suture is wound onto one or more of the panels and the folder package is folded and locked to securely maintain the needle and suture in the panel. Folder packages for surgical needles and sutures are illustrated and disclosed in the following patents which are incorporated by reference: U.S. Pat. Nos. 4,126,221, 4,120,395 and 5,555,976.

Another type of conventionally used suture package is a molded plastic tray package having a central floor surrounded by an outer winding channel for receiving and retaining a suture, e.g., an oval channel. This type of package typically has a centrally located needle park molded into the package. A surgical needle mounted to a surgical suture is typically packaged in the winding channel by initially mounting the surgical needle in the needle park and then winding the suture in the channel. Winding is typically accomplished by mounting the tray package in a fixture and rotating the fixture and mounted package. A cover may be mounted to the top of the winding channel package, or the package may have molded retainer elements, in order to maintain the suture in the channel. Suture tray packages having winding channels are illustrated in the following which are incorporated by reference: U.S. Pat. Nos. 4,967,902, 5,213,210 and 5,230,424.

Surgical needles and sutures are typically sold by the manufacturer as sterile products. In order to sterilize a packaged surgical needle and suture, it is first necessary to place the primary package into an outer package. The outer package is then sealed and functions as a biobarrier to pathogens, in particular, bacteria. The outer packages are often referred to in this art as envelopes or pouches, and the biobarriers are often referred to as microbial barriers. There are various types of conventional materials which are useful to construct these outer packages, including foil laminates, polymer films, TYVEK® spun polymer films and the like. There are a variety of conventional processes which can be used to sterilize packaged surgical needles and sutures including autoclaving, radiation sterilization and ethylene oxide sterilization. In general, the packaging material utilized for the outer package is selected on the basis of the sterilization technique utilized and the material of construction of the medical device.

Ethylene oxide sterilization is a sterilization process of choice for many medical devices. In a conventional ethylene oxide sterilization process for medical devices, the packaged devices contained in sealed outer envelopes or pouches are initially subjected to a vacuum, next to a predetermined level of water vapor, and then to a conventional ethylene oxide gas sterilant for a predetermined time at a predetermined temperature. The cycle is calculated to effectively kill off any pathogenic bioburden with an acceptable safety factor. At the end of the sterilization phase of the cycle, the packages are exposed to a vacuum sufficient to effectively remove the sterilant gas from the interiors of the envelopes or pouches along with any sterilant gas residues from the packages and the medical devices, thus completing the sterilization cycle. Since the moisture and the sterilant gas must have access to the interior of the outer package and the inner primary package containing the medical device, it is typically necessary to have some sort of gas permeable material present in the outer package to allow air, water vapor and sterilant gas to enter and exit the outer package. A conventional outer package (envelope or pouch) for use with ethylene oxide sterilization processes typically has a top clear polymer film which is gas impervious. The clear film is sealed or bonded about its periphery to a bottom microbial barrier member constructed of paper or a film of TYVEK® spun polymer (or an equivalent) which is gas permeable. Moisture and sterilant gas can move across the microbial barrier member into and out of the outer package.

Certain types of medical devices, such as surgical sutures, are designed to absorb when implanted into the human body. These absorbable sutures are made from conventional, widely known absorbable polymers which are moisture sensitive. In order to maintain the strength and integrity of the absorbable medical devices and prevent degradation while being shipped, or stored prior to use, it is essential that the outer package be moisture impervious, i.e., hermetically sealed. Accordingly, the conventional gas permeable microbial barrier outer pouch packages cannot be used for absorbable medical devices. It is necessary to use an outer package which is impervious to water vapor and gases, such as a conventional polymer/metal foil laminate pouches typically referred to in this art as a "foil pouch".

It is desirable to sterilize packaged synthetic, absorbable medical devices, such as surgical sutures, using ethylene oxide sterilization processes. Radiation or high temperatures may adversely affect the absorbable polymers. However, sealed foil pouches are also impervious to sterilant gas. In order to compensate for this and utilize foil packages in ethylene oxide gas sterilization processes, processes have been developed using foil pouches having gas permeable or pervious vents (e.g., TYVEK® polymer). The gas permeable vents are mounted to an open end of the foil package and allow the passage of air, water vapor and sterilant gas into the interior of the package. After sterilization, the foil package is sealed adjacent to the vent, and the vent is cut away or otherwise removed, thereby producing a gas impervious hermetically sealed package. Yet another type of foil package having a vent is a pouch-type package having a vent mounted adjacent to an end of the package, wherein the vent is sealed to one side of the package creating a vented section. After sterilization, the package is sealed adjacent to the vent, and the package is cut away for the vented section. This vented package will be described in more detail hereinbelow.

Alternatively, processes have been developed for sterilizing foil packages without the use of gas permeable vents. This is done by sealing the foil package substantially about its periphery (e.g., on three sides) but leaving a portion of the package open, typically the top end, as a pathway for the sterilant gas, etc. This type of process is known as an "open vent" process. In an open vent process, after the sterilization cycle has been completed the opening in each package is sealed under aseptic conditions, providing for a hermetically sealed foil package having a sterile interior. An example of such a process is disclosed in U.S. Pat. No. 3,815,315 which is incorporated by reference. Another example of an open vent sterilization process useful for an open vent package is contained in U.S. Pat. No. 5,464,580 which is incorporated by reference.

It is known to form foil packages in a multiple pack format to contain multiple suture packages. These outer packages have multiple cavities, for example, eight cavities. A surgical suture package is placed in each cavity, and each cavity is sealed about its periphery on three sides, leaving an opening(i.e., an open vent) in communication with each cavity. After ethylene oxide sterilization, the openings are subsequently sealed aseptically, and the packages are separated into unitary packages. Such sterilization processes, foil packages and methods of forming the packages are disclosed in U.S. Pat. Nos. 5,464,580 and 5,623,810 which are incorporated by reference. Although such foil packages having multiple cavities are conventionally utilized, there are some disadvantages associated with their use. For example, in order to sterilize the multiple cavity packages, the pathway to each cavity must be kept open. Then, after sterilization, the packages must be maintained in aseptic environments prior to and during sealing. It is known that it is difficult and costly to maintain aseptic conditions in large volumetric facilities required for aseptic package storage and sealing. In addition, moisture must be precisely controlled in the aseptic environments to prevent degradation of bioabsorbable medical devices. It is also known that different levels of sterilization may be attainable with packages having microbial barriers versus packages having open vents.

Accordingly, there is a need in this art for a novel foil package, especially a multiple cavity foil package, for absorbable sutures and other medical devices which does not require aseptic sealing after sterilization and which can be immediately placed in a nonsterile environment prior to further processing for conversion to a hermetically sealed, sterile package. There is a further need for processes for sterilizing surgical sutures and needles and other medical devices in foil packages or pouches, in particular multiple cavity foil packages, without the need for aseptic processing.

DISCLOSURE OF THE INVENTION

Accordingly, it is an object of the present invention to provide a foil package for medical devices containing absorbable polymeric devices, in particular, absorbable surgical sutures.

It is a further object of the present invention to provide an outer, multiple cavity foil package for absorbable medical devices which can be sealed to effect a gas permeable and pathogen impervious package prior to sterilization, and which does not require aseptic processing after sterilization and during conversion to hermetically sealed unitary packages.

It is yet a further object of the present invention to provide a multiple cavity foil package having an interior gas permeable microbial barrier vent and channels in communication with the interior vent and the cavities.

It is still yet a further object of the present invention to provide a novel process for packaging and sterilizing medical devices, including absorbable sutures, packaged in multiple cavity outer foil packages.

Yet a further object of the present invention is a novel process for packaging absorbable suture packages in foil outer packages.

Therefore, a multicavity outer pouch package for absorbable medical devices such as surgical sutures is disclosed. The foil outer package has a first substantially flat planar member made from a foil. The first planar member has a plurality of cavities formed therein for receiving a medical device, preferably a packaged medical device, in each cavity. The first planar member has an outer periphery, an outer side and an inner side. The cavities are formed into the inner side of the first planar member. The outer pouch package also has a second substantially flat planar member made from a foil. The second planar member has an outer periphery, an outer side and an inner side. The second member also has an interior vent opening located therein. The vent opening has a periphery. A gas permeable microbial barrier membrane is mounted to the second planar member about the periphery of the opening. The inner surface of the first planar member is bonded to the inner surface of the second planar member about their outer peripheries to form a gas impermeable peripheral seal, and the inner surface of the first planar member is further bonded to the inner surface of the second inner surface about at least part of each cavity to form gas impermeable side seals adjacent to each cavity, said side seals having a first end and a second end, wherein the first end of each seal intersects the peripheral seal, thereby forming channels such that each cavity is in gaseous communication with the interior opening. After sterilization, the package is further sealed by providing a gas impervious seal about each opening to each cavity and completing the side seals as required, thereby providing for cavities which are completely hermetically sealed, sterile and gas impervious. The outer package is then processed into unitary packages by, for example, cutting. Each unitary package is hermetically sealed and gas impervious and contains a medical device such as a packaged suture in a sterile cavity.

Another aspect of the present invention is a multicompartment outer pouch package for medical devices such as absorbable sutures. The foil outer package has a first substantially flat planar member made from a foil. The first planar member has an outer periphery, an outer side and an inner side. The outer package also has a second substantially flat planar member made from a foil. The second planar member has an outer periphery, an outer side and an inner side. The second member also has an interior vent opening located therein. The vent opening has a periphery. A gas permeable microbial barrier membrane is mounted to the second planar member about the periphery of the opening. The inner surface of the first planar member is bonded to the inner surface of the second planar member about their outer peripheries to form a gas impermeable peripheral seal, and the inner surface of the first planar member is further bonded to the inner surface of the second inner surface to form compartments such that at least a part of least each compartment is bounded by gas impermeable side seals, said side seals having a first end and a second end, wherein the first end of each seal intersects the peripheral seal, thereby forming channels such that each compartment is in gaseous communication with the interior vent. After sterilization, the package is further sealed by providing a gas impervious seal about each opening to each compartment and completing the side seals as required, thereby providing for compartments which are completely sealed and gas impervious. The outer package is then processed into unitary packages by for example, cutting. Each unitary package is hermetically sealed and gas impervious and contains a medical device such as a suture package in a sterile compartment.

Yet another aspect of the present invention is an outer foil package for an absorbable medical device such as a surgical suture. The foil outer package has a first substantially flat planar member made from a foil. The first planar member preferably has a cavity formed therein for receiving a medical device in the cavity. The first planar member has an outer periphery, an outer side and an inner side. The cavity is formed into the inner side of the first planar member. The outer foil package also has a second substantially flat planar member made from a foil. The second planar member has an outer periphery, an outer side and an inner side. The second member also has an interior vent opening located therein. The vent opening has a periphery. A gas permeable microbial barrier membrane is mounted to the second planar member about the periphery of the opening. The inner surface of the first planar member is bonded to the inner surface of the second planar member about their respective outer peripheries to form a gas impermeable peripheral seal. The cavity is in gaseous communication with the interior vent opening. After sterilization, the package is further sealed by providing a gas impervious seal between the vent and the cavity as required, thereby providing for a cavity which is completely hermetically sealed and gas impervious.

Yet another aspect of the present invention is a method of packaging a medical device such as a suture package in an outer foil package. Initially, a first substantially planar member is provided. The first member has an inner side, an outer side and an outer periphery. Then, a plurality of cavities is formed in the inner side of said first planar member, said cavities being suitable for receiving a medical device. Next, a medical device such as a surgical suture package is inserted in each cavity. A second substantially planar member is provided having an outer periphery, an outer side and a top side. A vent hole having an outer periphery is cut into the interior of the second planar member, said hole being preferably centrally located therein. A gas permeable microbial barrier member is mounted over the opening, and sealed about the periphery of the vent opening, thereby providing a gas permeable microbial barrier vent. Then, the first and second planar members are aligned such that the outer peripheries are substantially in registration. Next, the inner sides of the planar members are sealed together to form a gas impervious outer peripheral seal and side seals adjacent to each cavity, such that each cavity is substantially bounded by gas impervious seals but has an internal opening in gaseous communication with the interior microbial barrier vent. Next, the package is sterilized with a gaseous sterilant. Then, the internal openings to each cavity are sealed with gas impervious seals such that each cavity is bounded by said gas impervious seals and is hermetically sealed. And, finally sterile unitary suture packages are formed from the sterile multicavity package by cutting the package adjacent to each cavity such that each hermetically sealed unitary package comprises a cavity bounded by gas impervious seals.

Yet another aspect of the present invention is a method of packaging medical devices in the above described packages utilizing compartments and not cavities.

Other features and advantages of the packages of the present invention will become more apparent from the following description and accompanying drawings.

BRIEF DESCRIPTION OF THE DRAWINGS

FIG. 6A is a top view of a package of the present invention after it has been converted into individual packages and scrap.

FIG. 8A is a top view of the package of FIG. 8 after the interior seal has been formed into the package providing individual hermetically sealed compartments.

DESCRIPTION OF PREFERRED EMBODIMENTS

Figure 1:
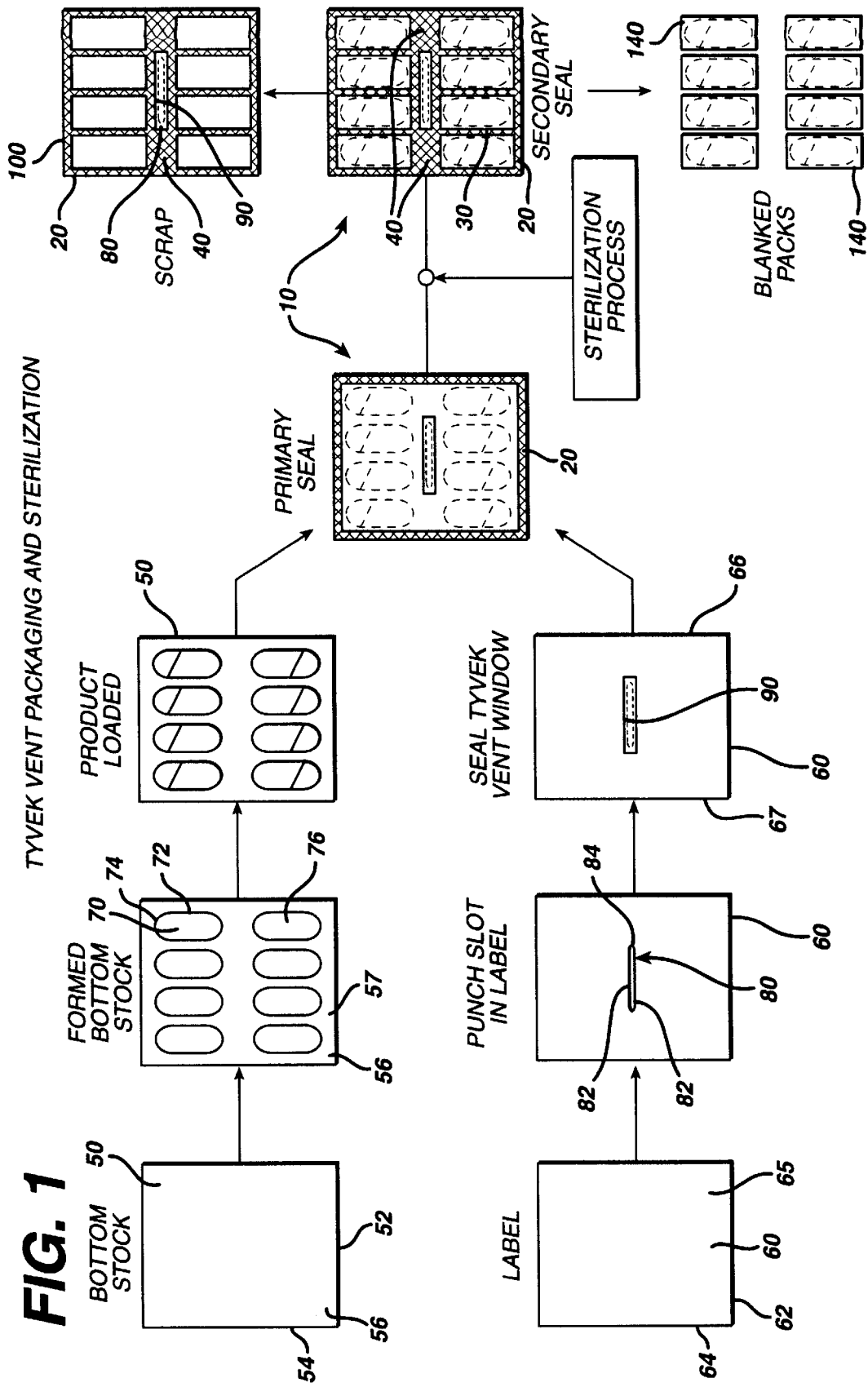
FIG. 1 is a flow diagram of a packaging process of the present invention.
Figure 2:
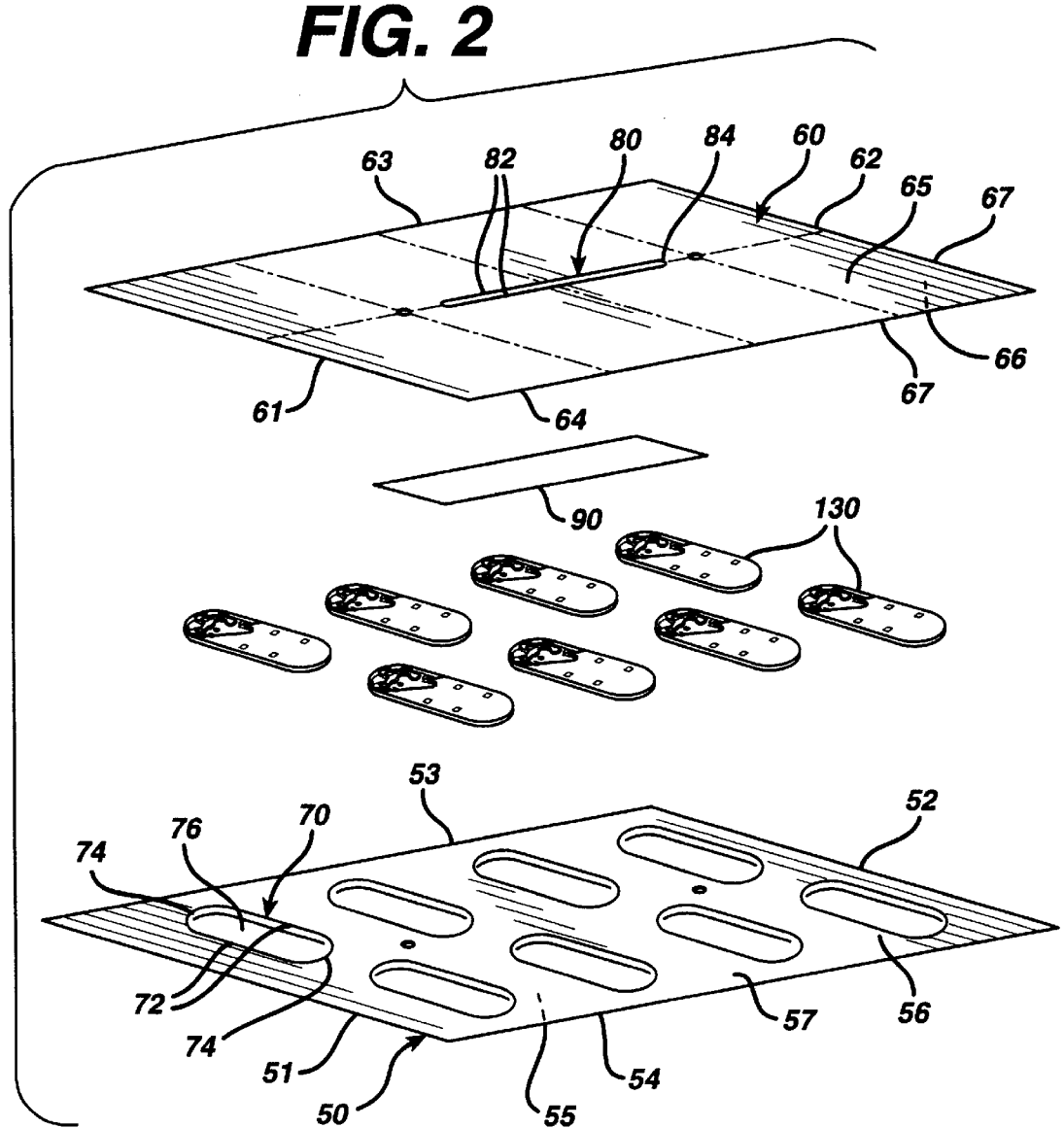
FIG. 2 is an exploded perspective view of the components of a vented multi-cavity package of the present invention, showing the top member, bottom member, microbial barrier, and individual suture packages.
Figure 3:
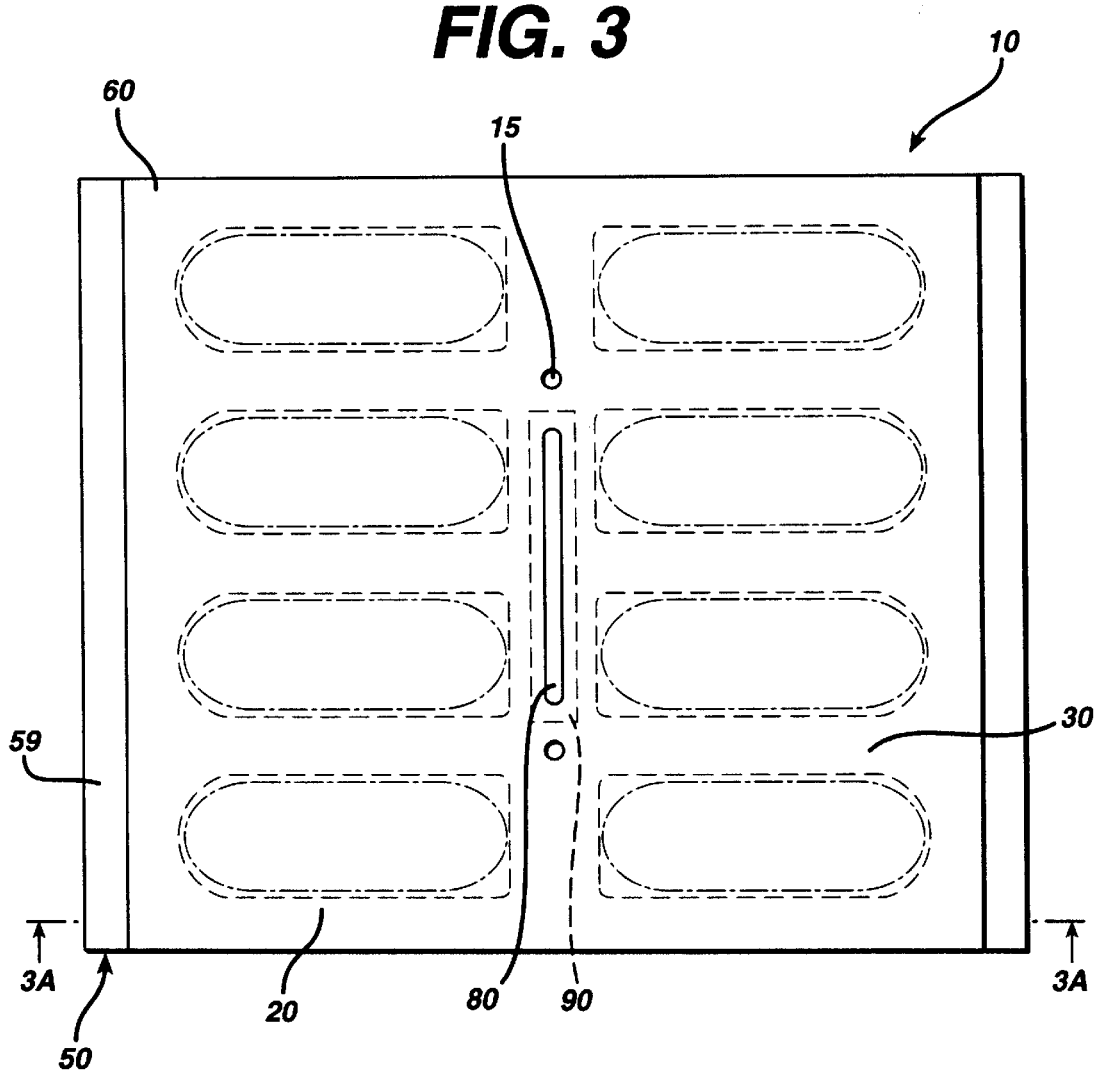
FIG. 3 is a top view of the package of the present invention before the primary outer peripheral seal has been completed; the cavities for receiving medical device packages are illustrated in phantom.
Figure 3A:
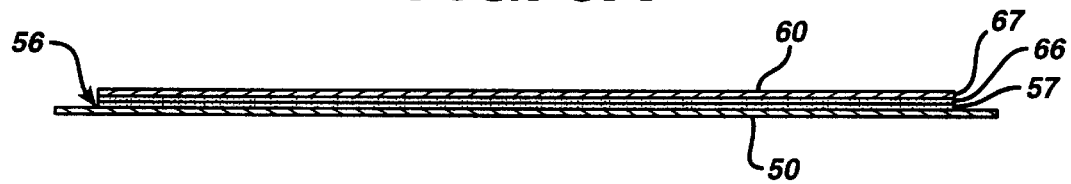
FIG. 3A is a partial cross-sectional view of the package of FIG. 3 along View Line 3A—3A illustrating the heat sealable coatings on the planar members.
Figure 4:
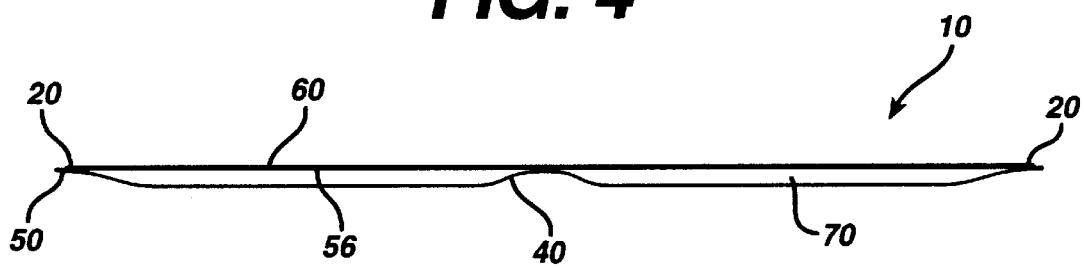
FIG. 4 is a side view of the package of FIG. 3.

The term "gas" as used herein is defined to have its customary meaning and to further include vapors such as water vapor. The terms "gas impervious" and "gas impermeable" as used herein are defined to mean impenetrable by gases and pathogens. The terms "gas permeable" and "gas pervious" as used herein are defined to mean penetrable by gases but not pathogens. The term "microbial barrier" as used herein is defined to mean a barrier which is gas permeable or pervious and impermeable by, or impervious to, pathogens.

The materials useful for constructing the packages of the present invention include conventional metal foil products often referred to as heat-sealable foils. The heat-sealable foils are typically a laminate of one or more layers of thermoplastic resins such as polyethylene, or other polyolefins or equivalent polymeric materials coated onto a metal foil substrate, such as aluminum. The application of heat to specific sections of such a foil laminate will cause the polymeric coating to melt and thereby fuse with or into a similarly heat treated portion of a polymeric film on another piece of foil laminate. These types of foil materials are disclosed in U.S. Pat. No. 3,815,315 which is incorporated by reference. Another type of foil laminate which may be utilized is a foil laminate referred to in this art as a peelable foil. The peelable foil laminate similarly utilizes a foil metal substrate, such as aluminum, to which one or more polymeric coating has been applied. The inner polymeric coating is similarly heat sensitive and melts to fuse with the polymeric coating on another piece of the metal foil thereby forming a heat seal. The bond strength between the fused coating material and the foil metal substrates is such that the two layers may be separated by pulling apart the fused laminates thereby causing one or both of the polymeric layers to become removed from a metal substrate. Examples of such peelable foil packaging and substrates are disclosed in U.S. Pat. No. 5,623,810, which is incorporated by reference. If desired, conventional non-metallic polymer films in addition to metal foil may be used to form the packages of the present invention. The films are polymeric and include conventional polyolefins, polyesters, acrylics and the like combinations thereof and laminates. The polymeric films will be substantially gas impermeable and may be coated with conventional coatings, for example mineral coatings which decrease or reduce gas intrusion. The packages of the present invention may also be constructed of a combination of polymer and metal foils.

The microbial membranes useful in the packages of the present invention include conventional gas permeable microbial membranes such as TYVEK® spun polymeric material (polyethylene), paper, polymer films and the like and equivalents thereof.

The types of medical products which may be packaged in the packages of the present invention include any types of absorbable and non-absorbable medical devices, including sutures, tissue fasteners such as tacks, meshes, bone pins, suture anchors, bone screws, staples, and the like. Preferably the medical devices will be individually packaged in primary packages prior to packaging in the outer packages of the present invention. It is particularly preferred to use the outer packages of the present invention for suture packages. The absorbable medical devices are typically made from generally known, conventional absorbable/resorbable polymers such as glycolide, lactide, co-polymers of glycolide or mixtures of polymers such as polydioxanone, polycaprolactone and the like and equivalents thereof. It is known that if medical devices made from these absorbable polymers come into contact with water vapor prior to the time that they are to be used, they may tend to rapidly deteriorate and lose their strength. In particular, the desirable property of in-vivo tensile strength retention for sutures will be rapidly lost if the products are exposed to moisture for any significant period of time prior to use. In addition, the products are also sensitive to radiation and heat. Accordingly, as mentioned previously, it is preferred to sterilize such absorbable polymeric medical devices using conventional sterilant gases, in particular ethylene oxide gas.

Figure 10:
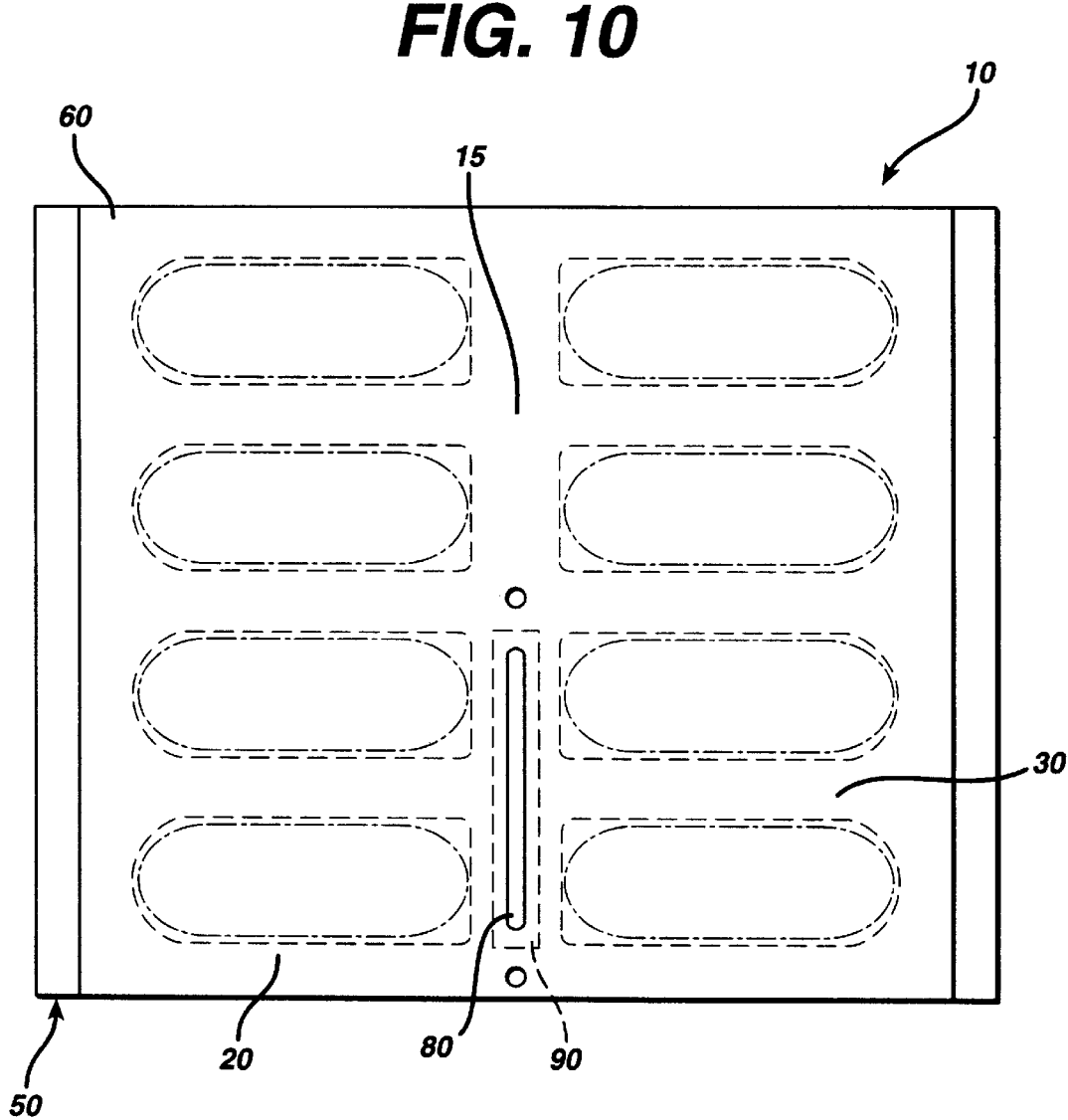
FIG. 10 is a top view of a multicavity package of the present invention prior to completion of peripheral seals containing an off-center vent in the top planar member.

Referring first to FIGS. 1–7, a multi-cavity foil package 10 of the present invention is illustrated. The package is seen to have first planar member 50 having opposed sides 51 and 52 and opposed sides 53 and 54. First planar member 50, also known as the bottom stock member, is seen to be rectangularly shaped and to have outer side 55 and inner side 56. Member 50 may have any desire shape including square, oval, circular, polygonal, etc., and combinations thereof. Inner side 56 is seen to have polymeric heat sealable coating 57. The package 10 is also seen to have second planar member 60 having opposed sides 61 and 62 and opposed sides 63 and 64. The second planar member 60, also known as the label member, is seen to be substantially rectangularly shaped, but may have any geometric configuration, similar to member 50. Member 60 is also seen to have outer side 65 and inner side 66. Heat sealable coating 67 is seen to be coated onto bottom side 66 of planar member 60. As seen in FIGS. 1, 3, 4, 5, and 6, the first planar member 50 is seen to have a plurality of optional cavities 70 formed therein. The cavities 70 are seen to have sides 72, opposed ends 74, and bottom 76. The cavities 70 are formed in a conventional manner using, for example, conventional dies and plugs and/or compressed gas, for forming the foil into the shapes as defined by the cavities. The cavities 70 preferably have an oval-type shape as illustrated, however, other types of configurations are also possible depending on the size and shape of the medical device and/or primary package to be packaged. These configurations include circular configurations, square, rectangular, polygonal, and combinations thereof. The cavities 70 are formed into the inner side 56 of planar member 50 having the coating 57 such that the bottom 76 of the cavities 70 is below the bottom 56 of planar member 50. The second planar member 60 is seen to have vent opening 80. Opening 80 is seen to be preferably rectangularly shaped, having opposed major sides 82 and opposed minor sides 84. However, if desired, the vent opening 80 may have various types of geometric configurations, including circular, oval, rectangular, polygonal, and combinations thereof. Mounted to the vent opening 80 is the gas permeable microbial membrane 90. Although the vent opening 80 is preferably centrally located, the vent may be located in a position off-set from the center of the package, for example, adjacent to a side of the planar membrane as seen in FIG. 10. Vent opening 80 will have a sufficient size to effectively allow gases including gaseous sterilant to flow into and out of the package 10 to permit sterilization of the interior cavities 70 and medical devices contained therein. The size of vent opening 80 will depend upon the size of the cavities 80 and the types of medical devices contained therein. For example, with a package 10 having eight cavities 70 containing surgical suture packages, vent 80 will be about 0.22 square inches to about 0.88 square inches. However, it is preferable to make the vent as large as practicable, the restraints on size coming from economies realized when the vent is smaller resulting in material savings. It is particularly preferred to have a rectangular vent with dimensions of about ¼"×3.5" when using the package 10 for surgical sutures wherein the package 10 has eight cavities. Gas permeable membrane 90 may be mounted to either the outside 65 or the inner side 66 of member 60 although it is preferable to mount it to the inner side to coating 67. The membrane 90 will have a sufficient size to effectively cover the opening 80 when mounted therefor. The gas permeable microbial membrane 90 will typically be heat fused to the inner coating 57 of the inner side 56 of planar member 50, however, the gas permeable membrane 90 may be mounted to the member 50 by other conventional sealing or bonding methods including: ultrasonic, glues, sealants, and the like or equivalent thereof. Membrane 90 may also be mounted to outer side 55 of member 50. Membrane 90 may have any configuration including rectangular, square, circular and the like. Membrane 90 will have a sufficient porosity to effectively act as a biobarrier while allowing gas and water vapor to pass therethrough. The porosity will typically range from about 10 to about 635 Gurley Seconds.

Figure 5:
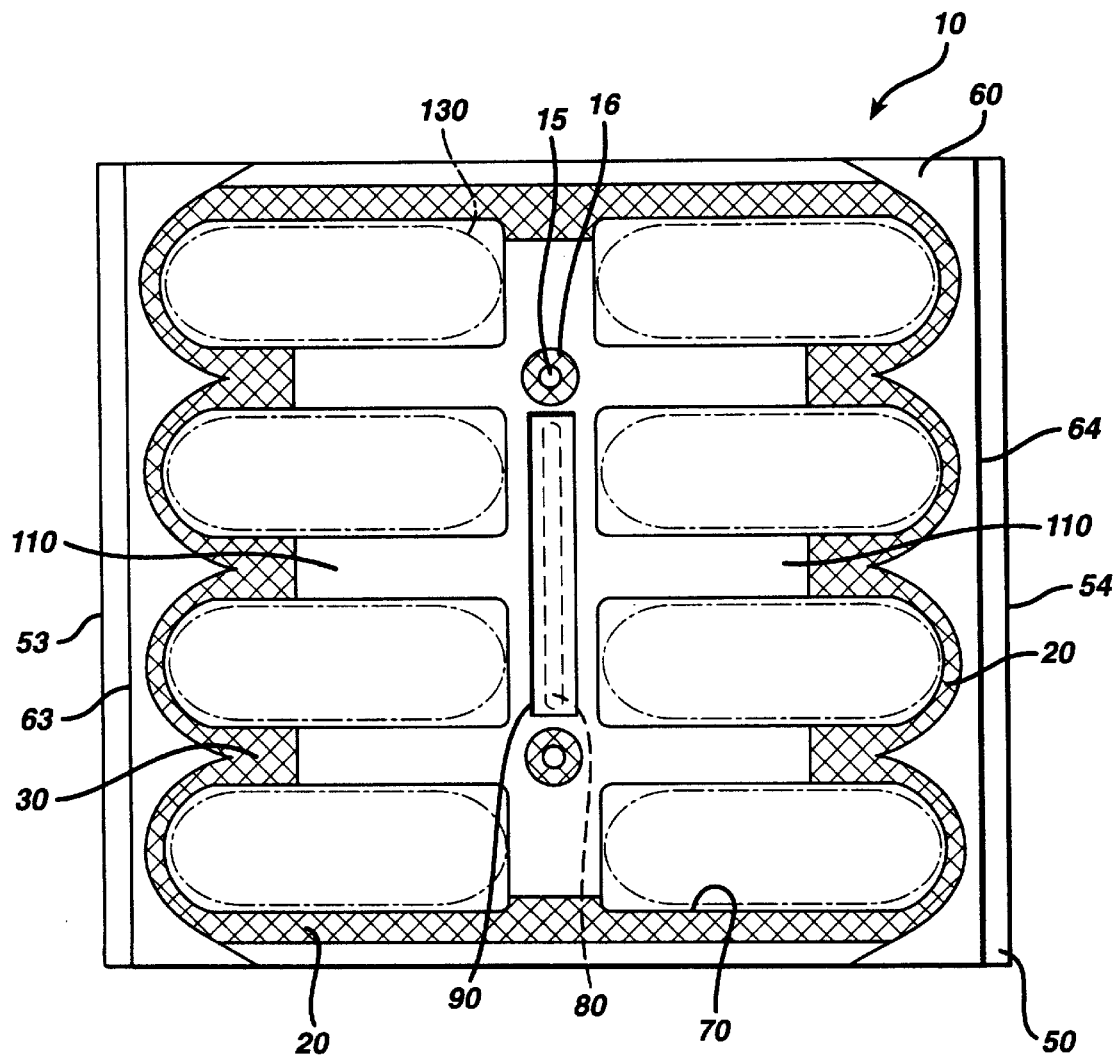
FIG. 5 is a top view of a multicavity package of the present invention after the primary peripheral seal and side seals have been formed; cavities and suture packages packaged in the cavities are illustrated in phantom lines.

Referring now to FIG. 5, the package 10 is seen to have peripheral seal 20 and side seals 30. The peripheral seal 20 may be configured to extend parallel to the sides of the planar members 50 and 60 or may be contoured to follow the shapes of cavities 70 or combinations thereof. For example, the peripheral seal 20 is seen to follow the configuration of the ends 74 of cavity 70. The side seals 30 are seen to extend from peripheral seal 20, partially between, and adjacent to the cavities 70. The package 10 is also seen to have the pilot holes 15 adjacent to opening 80. Pilot holes 15 extend through both planar member 50 and planar member 60 and are used to align both members together as well as to align the planar members and package 10 in various pieces of processing machinery. The area surrounding holes 15 is sealed by seals 16. It can be seen that although sides 51 and 52 of planar member 50 and sides 61 and 62 of planar member 60 are aligned and coextensive, planar member 50 is larger than member 60, such that sides 53 and 54 extend beyond sides 63 and 64 to form a flap 59. The combination of the peripheral seal 20 and the side seals 30 creates a plurality of channels or a manifold passageway 110 from vent 80 through barrier member 90 to the cavities 70. This manifold passageway allows sterilant gas to enter vent 80 and travel via the manifolded channels to the cavities 70 thereby allowing it to come into contact with the packages 130 or any other medical devices contained in the cavities 70, and also allows for the evacuation or removal of the sterilant gas from the interior of package 10 as well as for the removal of other conventional gases and vapors including ambient air, nitrogen, gaseous diluents, water vapor and the like.

Figure 6:
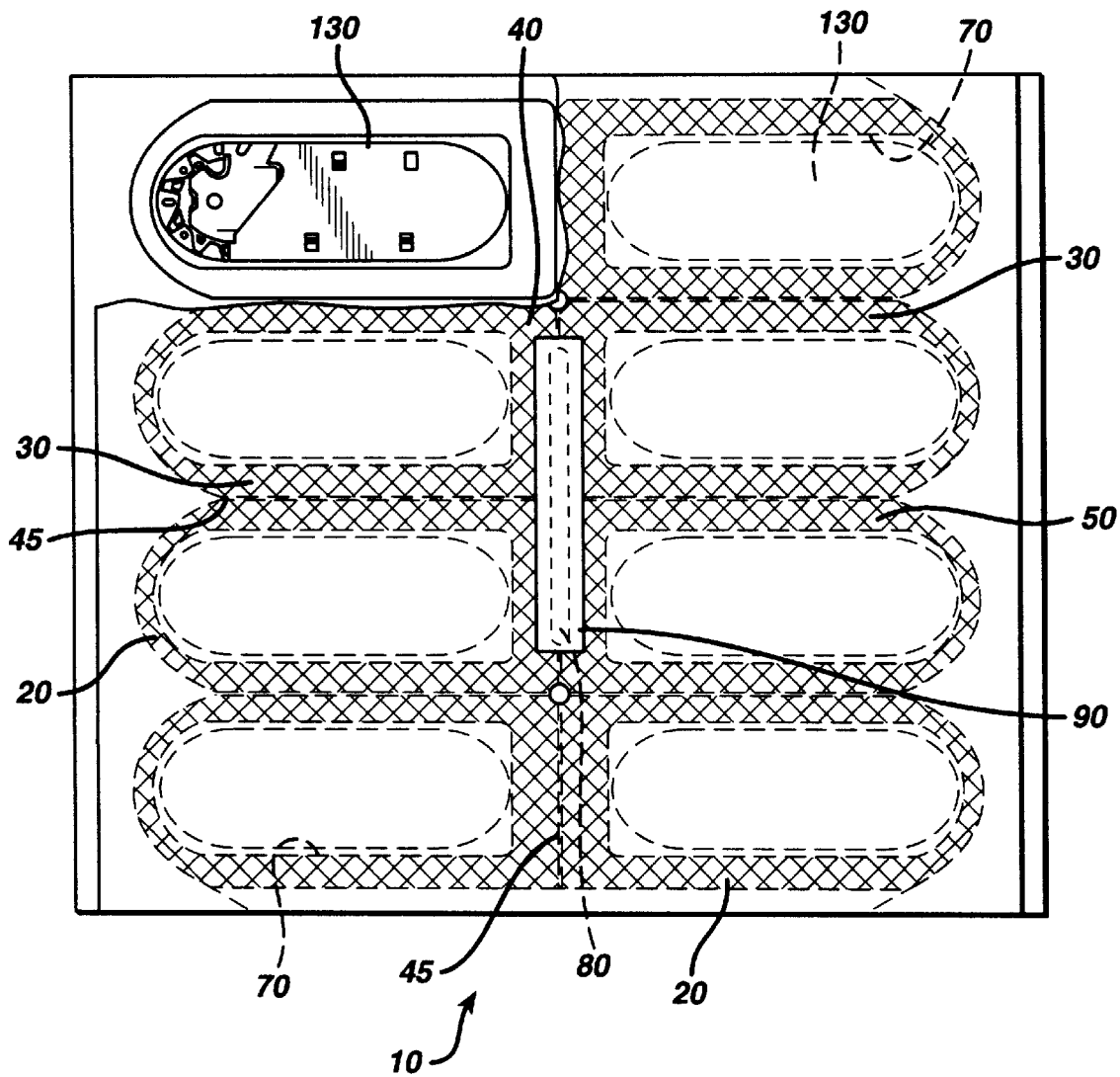
FIG. 6 is a top view of a multicavity package of the present invention after the secondary seal has been completed with a partial cut-away showing a cavity and suture package contained therein
Figure 7:
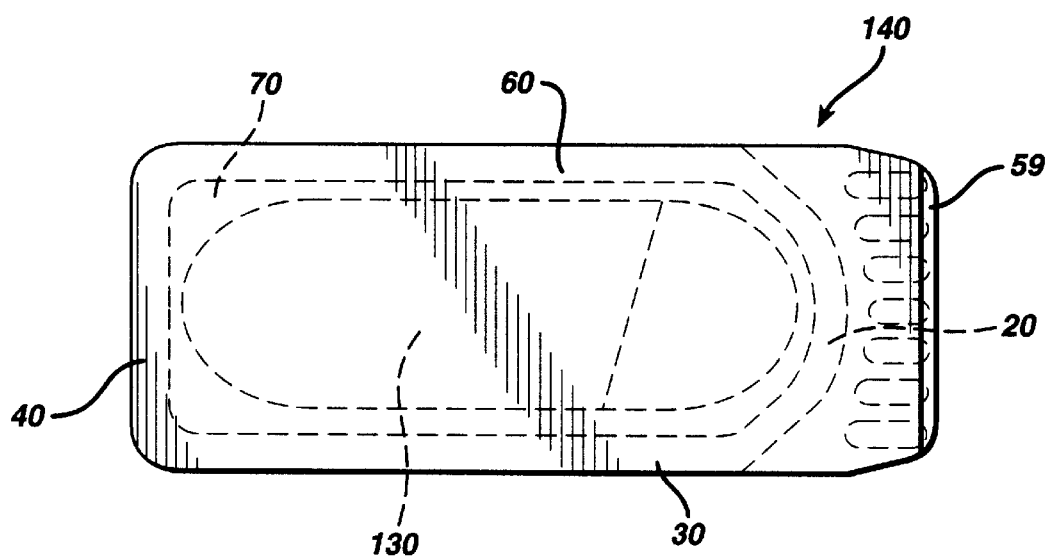
FIG. 7 is a top view of a unit package converted from the multicavity package of FIG. 6.

Referring now to FIG. 6, the interior seals 40 are illustrated. Seals 40 are processed into the package 10 after sterilization along with the optional grooves 45. Grooves 45 are believed to eliminate wrinkles in the foil planar members. The side seals 30 are simultaneously extended to interior seals 40 so that each cavity 70 is completely sealed off such that the cavities 70 are each maintained in a hermetically sealed gas impermeable package. This is typically done after sterilization as will be discussed below. The package 10 is then separated into unit packages 140 as seen in FIGS. 6 and 7 by die cutting the individual packages 140 from the package 10 such that each unitary package 140 contains a cavity 70 surrounded by a gas impermeable seal. The flaps 59 of packages 140 are seen to contain indentations 58 to facilitate opening of the package 140. As illustrated in FIG. 6A., the vent 80 and gas permeable material 90 along with scrap 100 are cut away and do not remain with the package 10 after the unit packages 140 have been cut away.

Referring now to FIG. 10, a package 10 of the present invention is illustrated wherein the vent opening 80 is offset and not centrally located. Although a central vent is preferred, it will be appreciated by those skilled in the art that the vent can be located anywhere within the package 10 and the manifolding of channels created by side seals 30 will be adjusted and arranged to have a gaseous pathway between the vent 80 and each cavity or compartment.

Figure 8:
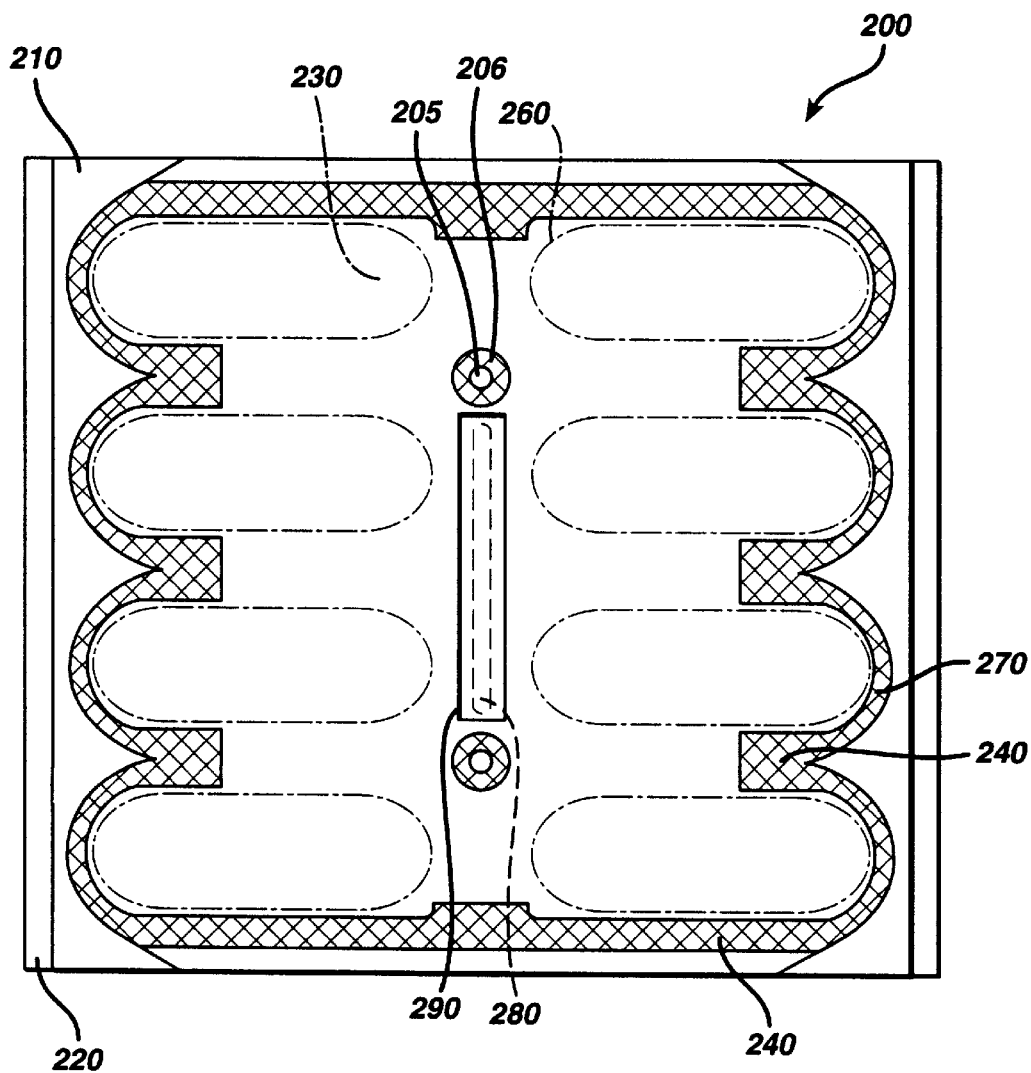
FIG. 8 is a top view of a package of the present invention which does not have cavities but has compartments; the package is shown after the peripheral seal and side seals have been formed.
Figure 9:
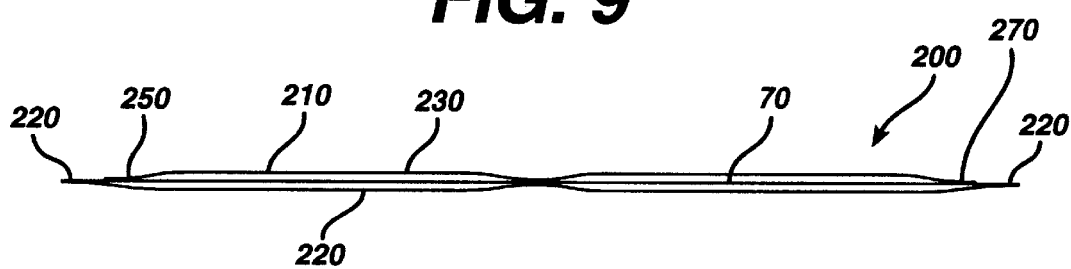
FIG. 9 is a side view of the package of FIG. 8.

Another embodiment of the package of the present invention is seen in FIGS. 8 and 9. The package 200 is seen to have top planar member 210 and bottom planar member 220. The upper planar member 210 is seen to have vent opening 280 and biobarrier membrane 290 covering vent opening 280. Member 210 is heat sealed to member 220 to form peripheral seal 270. Contained in the package 10 are medical devices, for example suture packages 260. Prior to sterilization, side seals 240 are formed by heat sealing to partition the package 10 into a plurality of compartments 230. Side seals 240 are typically formed at the same time that peripheral seal 270 is formed and intersect at one end the seal 270. After sterilization, the ends of the compartments are sealed by forming seal 250 into the package while also extending side seals 240 to intersect seal 250 (see FIG. 8A) thereby providing a hermetic seal about each compartment 230 prior to cutting the package 200 into unitary hermetically sealed packages. FIG. 9 illustrates a side view of the package of FIG. 8 showing the compartments 230. The package 200 is also seen to have pilot holes 205 surrounded by seals 206.

Figure 11:
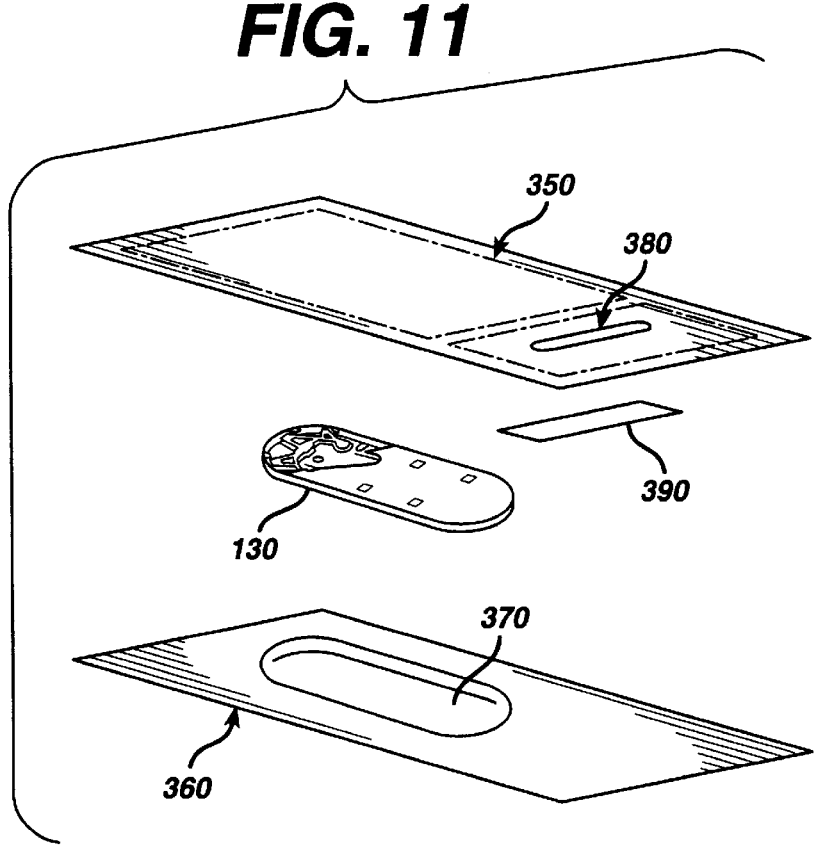
FIG. 11 is an exploded perspective view of an alternate embodiment of a package of the present invention having a single cavity for receiving a single medical device.
Figure 12:
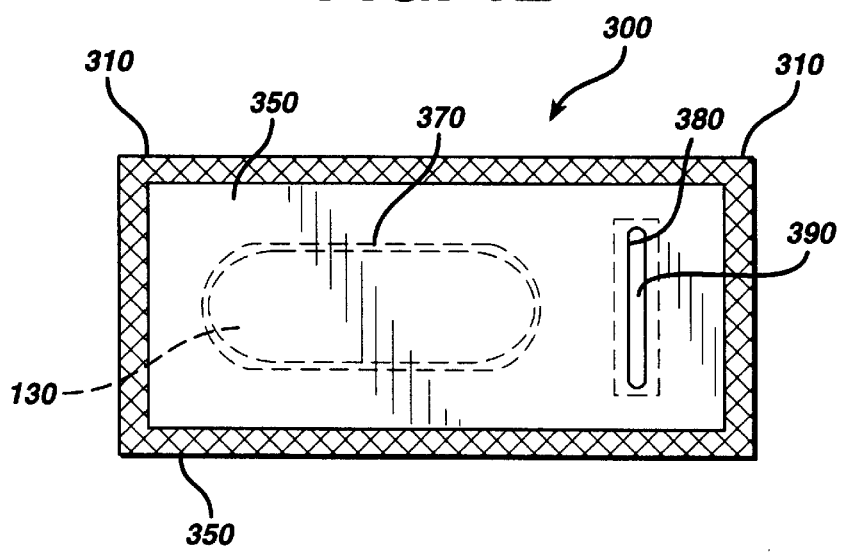
FIG. 12 is a top view of the package of FIG. 11 after assembly.
Figure 12A:
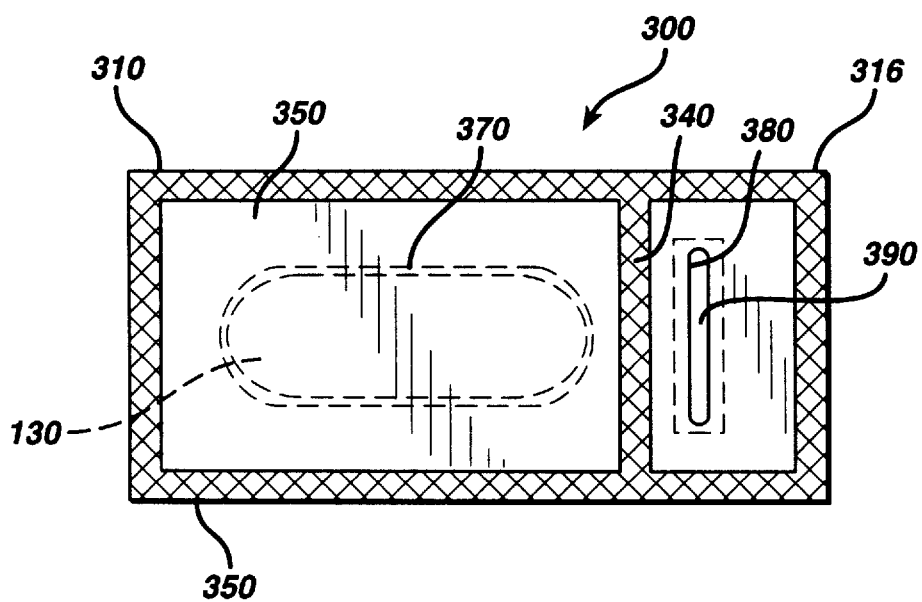
FIG. 12A is a top view of the package of FIG. 12 after sterilization and insertion of a seal between the vent and the rest of the package to create a hermetic seal about the cavity.

Yet another embodiment of the package of the present invention is illustrated in FIG. 11, FIG. 12 and FIG. 12A. The package 300 is a unitary package without multiple cavities or pouches. The package 300 is seen to have a cavity 370, a peripheral seal 310, upper planar member 350, lower planar member 360, and a vent opening 380 covered by biobarrier membrane 390. After sterilization a seal 340 adjacent to the vent 380 is formed into the package 300 by heat sealing thereby hermetically sealing the cavity 370 (See FIG.12A). Then, the vent 380 is cut away from the package 300 adjacent to the seal 340 to form a hermetically sealed unitary package.

It will be appreciated by those skilled in the art that the dimensions of the packages of the present invention along with the cavities and compartments will vary in accordance with the size of the medical devices to be packaged along with the types of packaging material and the types of packaging equipment which are utilized.

Figure 13:
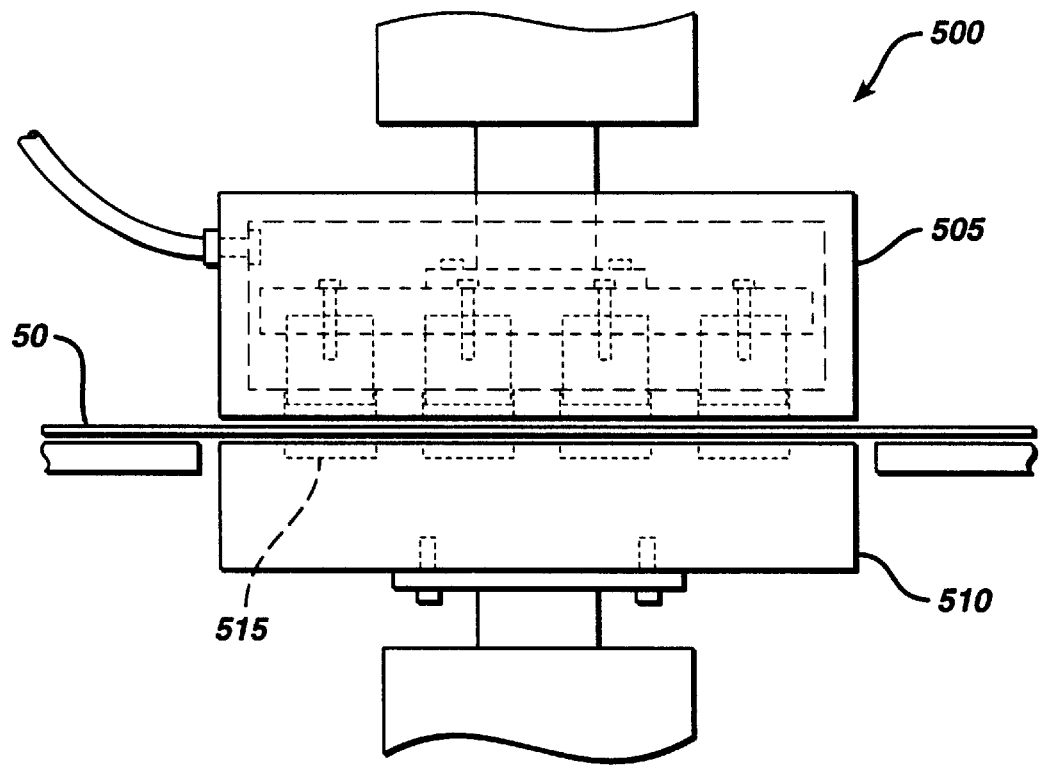
FIG. 13 is a side view of a packaging apparatus useful for forming cavities in a sheet of foil material.
Figure 14:
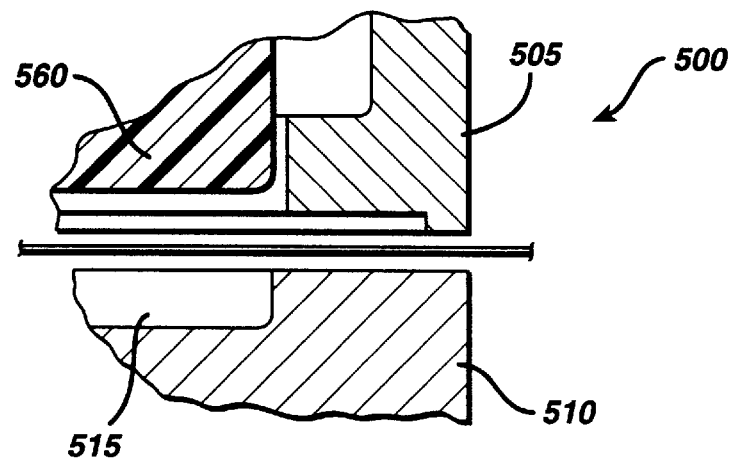
FIG. 14 is a partial cross-sectional view of the apparatus of FIG. 13 illustrating the plug and die used to form cavities in foil.
Figure 15:
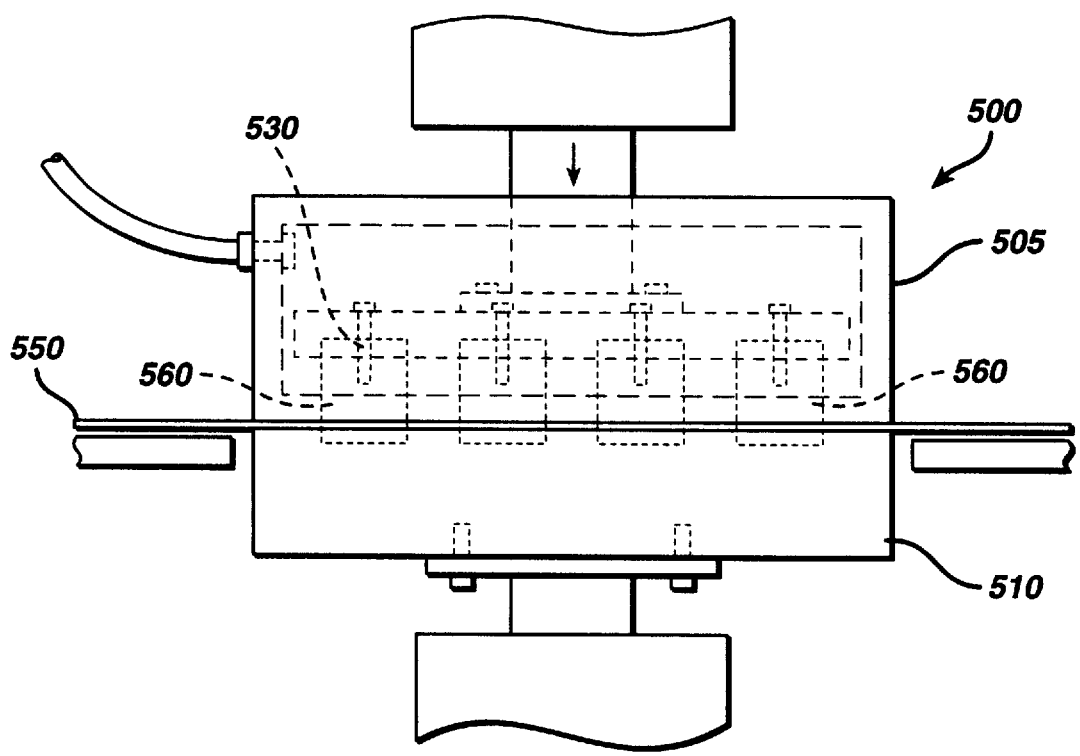
FIG. 15 is a side view of the of the apparatus of FIG. 12 illustrating the plugs extending into the dies to form the cavities in foil.
Figure 16:
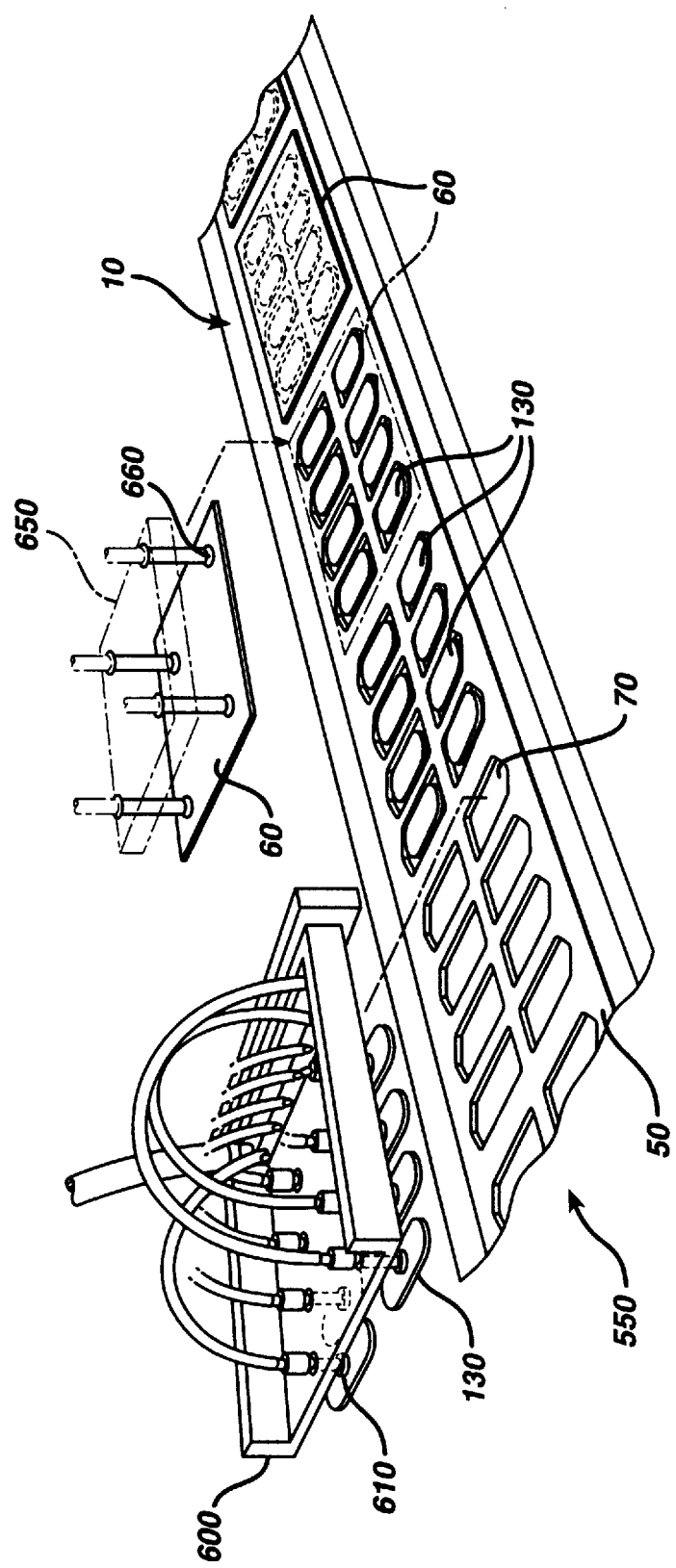
FIG. 16 is a perspective view of a packaging apparatus useful in assembling the packages of the present invention.

A process of the present invention for packaging absorbable medical devices, preferably packaged absorbable sutures, in the packages 10 of the present invention is illustrated in FIG. 1. As seen in FIG. 1, first planar members 50 (also referred to as bottom stock) are individually fed into a conventional multicavity foil apparatus 500 as seen in FIGS.13–15. Cavities 70 having roughly the shape of suture packages 130 are then formed in the inner side 56 of planar member 50. Printed foil stock having labeling is previously processed via a conventional cutting apparatus and cut into a plurality of second planar members 60. Next, a vent opening 80 is die cut into planar member 60 and biobarrier membrane 90 is sealed onto the inner side 66 of second planar member 60 about opening 80 to provide a biobarrier about vent opening 80. Then, medical devices such as suture packages 130 are loaded into the cavities 70 of a first planar member 50 such that one suture package 130 is loaded into each cavity 70 as illustrated in FIG. 16. Then, first and second planar members 50 and 60 are aligned using the pilot holes 15, and primary peripheral seal 20 and side seals 30 are formed by heat sealing the inner coatings 57 and 67 using conventional heat sealing equipment to form the manifold 100. Next, the package 10 containing the suture packages 130 is processed through a gaseous sterilant sterilization process, such as an ethylene oxide sterilization process as described below. After the ethylene oxide sterilization process, the sterile packages 10 may be stored in a dry, humidity-controlled room prior to final processing for secondary seal 40 and extensions of side seals 30. Secondary seal 40 is formed by heat sealing the coatings 67 and 57 to form interior seal 40 and extending side seals 30 to intersect seal 40, thereby providing a gas impermeable seal about each cavity 70, such that each cavity 70 is hermetically sealed. Next, the package 10 is die cut or blanked using conventional equipment into individual hermetically sealed packages 140, wherein each package 130 has a cavity 70 containing a suture package 130 wherein the suture package and cavity are surrounded by a gas impermeable seal. The packages 130 may then be further packaged in various types of shipping or display packages. After the cutting or blanking process, the remainder of the package 10 is discarded as scrap 100. The scrap 100 containing the vent 80 and biobarrier 90 is typically separated from the packages 140 either manually or using conventional machinery.

Referring now to FIGS. 13–16, apparatuses useful to form the packages of the present invention are illustrated. The apparatuses are further described in U.S. Pat. No. 5,623,810 which is incorporated by reference. Cavity forming apparatus 500 is seen to have upper frame 505 and lower frame 510. Lower frame 510 is seen to have a plurality of cavities 515 therein. Foil first planar members 50 are seen to be placed between frames 505 and 515 of apparatus 500. Initially a jet of compressed air through nozzles 530 is used to deform the foil planar member 50 into the cavities 515. Then, as seen in FIG. 10, frame 505 containing plug members 560 is moved downward with respect to stationery frame 510 such that the plug members 560 engage the foil member 50 to further conform the foil more precisely to the shape of the cavities 515. Next, as seen in FIG. 16, frame 600 having manifolded vacuum pick-up units 610, is utilized to place medical devices such as packaged needles and sutures 130 into the cavities 70 of each first planar member 50. Next, the frame 650 having vacuum pick-up units 660 extending therethrough, is utilized to pick up a precut planar second member 60 and place it on top of and in registration with a first member 50 to form the package 10 prior to heat sealing and the formation of the peripheral and secondary seals.

A preferred embodiment of an ethylene oxide sterilization process useful for the packages 10 of the present invention is described below, although any conventional ethylene oxide gas process my be used which is sufficient to effectively sterilize a packaged medical device. Those skilled in the art will appreciate that although ethylene oxide gas is a preferred sterilant gas, any sterilant gas may be used with the packages 10 of the present invention. After the package 10 has been formed with the peripheral seal 20 and side seals 30 to form the manifold 100, the packages 10 are then placed into a conventional ethylene oxide sterilization unit. Prior to the start of the cycle, the sterilizer is heated to an internal temperature of about 25° C. Next, a vacuum is drawn on the sterilization unit to achieve a vacuum of approximately 1.8 to 6.0 kpa. Steam is then injected to provide a source of water vapor for the product to be sterilized. The packages 10 are exposed to water vapor in the sterilizer for a period of time of about 60 minutes to about 90 minutes. Following the humidification portion of the cycle, the sterilizer is pressurized by the introduction of dry nitrogen gas to the pressure of between about 46 and 48 kPa. When the desired pressure is reached, pure ethylene oxide is introduced into the sterilization unit until the pressure reaches about 95 kpa. The ethylene oxide sterilant gas is maintained in the sterilization unit for about 360 to about 600 minutes for surgical sutures. The time required to sterilize other medical devices may vary depending on the type of product and the packaging. The ethylene oxide sterilant gas is then evacuated from the sterilization unit and the vessel is maintained under vacuum at a pressure of approximately 0.07 kpa for approximately two hours in order to remove residual moisture and ethylene oxide from the sterilized sutures. The pressure in the sterilizer is then returned to atmospheric pressure at a temperature of about 21° C. to about 32° C. The product in the packages 10 is then dried by exposing the packages 10 to dry nitrogen and vacuum over a number of cycles sufficient to effectively remove residual moisture and water vapor from the product and packages. The packages are then removed from the sterilizer and may be stored in a humidity controlled storage area prior to processing into unitary packages. It is interesting to note that the storage of the multi-cavity packages prior to processing into unitary packages does not have to be in an aseptic environment, only humidity controlled.

Figure 17:
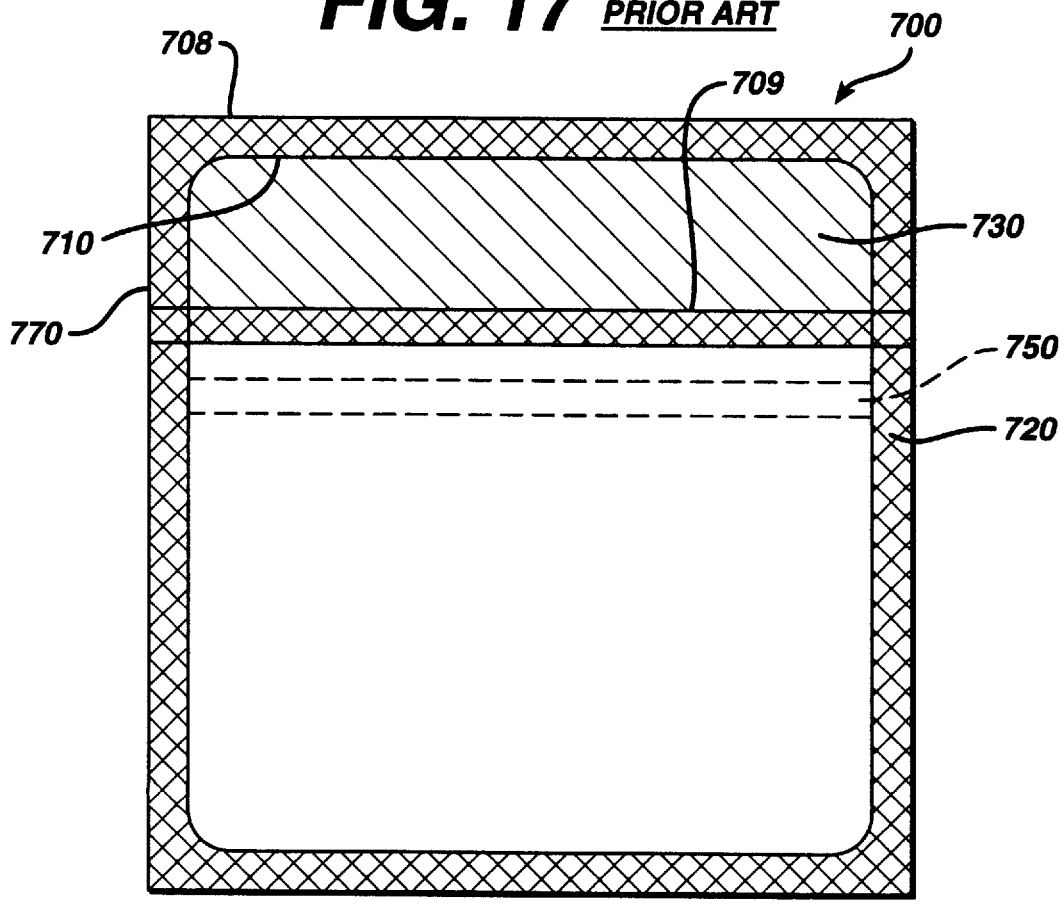
FIG. 17 is a top view of a foil pouch of the prior art having a vent.

A package of the prior art having a vent is seen in FIG. 17. The package 700 is seen to have upper foil member 705, lower foil member 706 and peripheral seal 720. One edge 708 of the member 706 is seen to extend substantially beyond the edge 709 of upper member 707 such that a flap 770 of foil is formed. The package 700 is seen to have a biobarrier vent 730 mounted on top of the flap 770 and edge 709, and sealed to lower flap 770 and edge 708 with seal 790. After medical device is inserted into the package 700, the vent is additionally sealed to member 706 around the edge 708 to seal off the package and allow the vent 730 to act as a biobarrier. After sterilization a secondary seal 750 illustrated in phantom is made adjacent to the vent member and the vent member and bottom piece of package are cut away to form a hermetically sealed sterile package. It is known that this type of package has several disadvantages including the fact that it is difficult to assemble the package in a secure gas impermeable manner.

In using the outer packages and processes of the present invention for multi-cavity absorbable suture or medical device packaging, it is now possible to gas sterilize the contents of each cavity of a multicavity foil and form hermetically sealed sterile unit packages without the need for a separate aseptic sealing step. The use of a central vent eliminates the need for aseptic processing thereby greatly improving the efficiency of the process and minimizing or eliminating the efforts required to prevent contamination during aseptic processing.

Although this invention has been shown and described with respect to detailed embodiments thereof, it will be understood by those skilled in the art that various changes in form and detail thereof may be made without departing from the spirit and scope of the claimed invention.

We claim:

1. A foil outer package for medical device packages, comprising:
   a first substantially planar member comprising a foil, said planar member having at least two cavities formed therein for receiving a medical device in each cavity, wherein said planar member has an outer periphery, an outer side and an inner side;
   a second substantially flat planar member comprising a foil, said second planar member having an outer periphery, an outer side and an inner side, said second member also having at least one vent opening therein, each said opening having a periphery;

a gas permeable microbial barrier membrane mounted to the second planar member about the periphery of each vent opening;

wherein the first planar member is mounted to the second planar member such that the outer peripheries are substantially in alignment, the inner surface of the first planar member being bonded to the inner surface of the second planar member adjacent to the outer peripheries of the planar members to form a gas impermeable peripheral seal, and the inner surface of the first planar member being further bonded to the inner surface of the second inner surface about each cavity to form a gas impermeable side seal adjacent to each cavity, said side seals having a first end and a second end, wherein the first end of each seal intersects the peripheral seal and the second end extends at least partially between adjacent cavities, thereby forming a manifold such that each cavity is in communication with the vent opening.

2. The package of claim 1 wherein each cavity has a shape selected from the group consisting of rectangular, oval, circular, square, polygonal, and combinations thereof.

3. The package of claim 1 wherein each cavity contains a medical device.

4. The package of claim 3 wherein the medical device comprises a surgical suture and surgical needle mounted thereto.

5. The outer package of claim 1 wherein the interior of the package is sterile.

6. The package of claim 4 wherein the suture and needle are in a package.

7. The package of claim 4 wherein the suture comprises an absorbable polymer.

8. The package of claim 1 wherein the package has an additional seal adjacent to each cavity, said seals intersecting the second end of each side seal and the peripheral seal, thereby hermetically sealing off each cavity such the cavities are no longer in communication with the central vent and each cavity is gas impervious and hermetically sealed.

9. The package of claim 7 wherein the package is cut into hermetically sealed unitary packages, each unitary package comprising a cavity.

10. The package of claim 1 wherein the vent opening is centrally located.

11. The package of claim 1 wherein the microbial barrier member is mounted to the interior of the second planar member.

12. The package of claim 1 wherein the vent opening has a shape selected form the group consisting of rectangular, square, round oval, polygonal and combinations thereof.

13. The package of claim 1 further containing at least one alignment hole therethrough surrounded by a seal.

14. The package of claim 1 wherein the outer periphery of the second planar member extends beyond the outer periphery of the first planar member, thereby forming at least one flap.

15. The package of claim 8 wherein the package has been cut to comprise at least two individual hermetically sealed packages, wherein each package comprises a cavity; and, scrap.

16. The package of claim 1 wherein the foil is selected from the group consisting of metal foil, and gas impermeable polymer film and combinations thereof.

17. The package of claim 16, wherein the foil comprises an inner heat seal coating.

18. A foil outer package for medical device packages, comprising:

a first substantially planar member comprising a foil, wherein said planar member has an outer periphery, an outer side and an inner side;

a second substantially flat planar member comprising a foil, said second planar member having an outer periphery, an outer side and an inner side, said second member also having at least one vent opening therein, each said opening having a periphery;

a gas permeable membrane mounted to the second planar member about the periphery of each vent opening;

wherein the first planar member is mounted to the second planar member such that the outer peripheries are substantially in alignment, the inner surface of the first planar member being bonded to the inner surface of the second planar member adjacent to the outer peripheries of the planar members to form a gas impermeable peripheral seal, and the inner surface of the first planar member being further bonded to the inner surface of the second inner surface to form at least two compartments bounded by gas impermeable side seals adjacent to each compartment, said side seals having a first end and a second end, wherein the first end of each seal intersects the peripheral seal and the second end extends at least partially between adjacent compartments, thereby forming a manifold such that each compartment is in communication with the at least one vent opening.

19. The package of claim 15 wherein compartment has a shape selected from the group consisting of rectangular, oval, circular, square, polygonal, and combinations thereof.

20. The package of claim 15 wherein each compartment contains a medical device.

21. The package of claim 15 wherein the medical device comprises a surgical suture and surgical needle.

22. The outer package of claim 15 wherein the interior of the package is sterile.

23. The package of claim 21 wherein the surgical suture and needle are in a package.

24. The package of claim 21 wherein the suture comprises an absorbable polymer.

25. The package of claim 15 wherein the package has an additional seal adjacent to each compartment, said seals intersecting the second end of each side seal and the peripheral seal, thereby hermetically sealing off each compartment such the compartments are no longer in communication with the central vent through the manifold and each compartment is gas impervious and hermetically sealed.

26. The package of claim 25 wherein the package is cut into hermetically sealed unitary packages, each unitary package comprising a compartment.

27. The package of claim 15 wherein the vent opening is centrally located.

28. The package of claim 15 wherein the microbial barrier member is mounted to the interior of the second planar member.

29. The package of claim 15 wherein the vent opening has a shape selected form the group consisting of rectangular, square, round, oval, polygonal and combinations thereof.

30. The package of claim 15 further containing at least one alignment hole therethrough surrounded by a seal.

31. The package of claim 15 wherein the outer periphery of the second planar member extends beyond the outer periphery of the first planar member, thereby forming at least one flap.

32. The package of claim 25 wherein the package has been cut to comprise at least two individual hermetically sealed packages, wherein each individual package comprises a compartment; and, scrap.

33. The package of claim 18 wherein the foil is selected from the group consisting of metal foil, gas impermeable polymer film and combinations thereof.

34. The package of claim 18, wherein the foil comprises an inner heat seal coating.

35. A foil outer package for a medical device package, comprising:

a first substantially planar member comprising a foil, said planar member having a cavity formed therein for receiving a medical device, wherein said planar member has an outer periphery, an outer side and an inner side;

a second substantially flat planar member comprising a foil, said second planar member having an outer periphery, an outer side and an inner side, said second member also having an interior vent opening therein, each said opening having a periphery;

a gas permeable membrane mounted to the second planar member about the periphery of the vent opening;

wherein the first planar member is mounted to the second planar member such that the outer peripheries are substantially in alignment, the inner surface of the first planar member is bonded to the inner surface of the second planar member adjacent to the outer peripheries of the planar members to form a gas impermeable peripheral seal such that the cavity is in communication with the vent opening.

36. The package of claim 23 wherein the cavity has a shape selected form the group consisting of rectangular, oval, circular, square, polygonal, and combinations thereof.

37. The package of claim 23 wherein the cavity contains a medical device.

38. The package of claim 25 wherein the medical device comprises a surgical suture and surgical needle mounted thereto.

39. The outer package of claim 23 wherein the interior of the package is sterile.

40. The package of claim 26 wherein the suture and needle are in a package.

41. The package of claim 26 wherein the suture comprises an absorbable polymer.

42. The package of claim 23 wherein the package has an additional seal adjacent to the cavity, said seal intersecting the peripheral seal, thereby hermetically sealing off each cavity such the cavity is no longer in communication with the vent and the cavity is gas impervious.

43. The package of claim 29 wherein the package is cut away form the vent to form a hermetically sealed unitary package.

44. A method of packaging a medical device in an outer foil package, said method comprising:

providing a first substantially planar member, said member having an inner side, an outer side and an outer periphery;

forming a plurality of cavities in said first planar member, said cavities suitable for receiving a surgical suture package, said cavities formed on the inner side of the planar member;

inserting a medical device in each cavity;

providing a second substantially planar member having an outer periphery, an outer side and a top side;

cutting a hole having an outer periphery into the second planar member, said hole centrally located therein;

mounting a gas permeable member over the opening, and sealing the member about the periphery of the opening, thereby providing a central vent;

aligning the first and second planar members such that the outer peripheries are substantially in registration;

sealing the inner sides of the planar members to form an outer gas impervious outer seal, and sides seals adjacent to each cavity, such that each cavity has an opening in communication with the central vent;

sealing off the openings in each cavity such that the cavity is bounded by gas impervious seals thereby hermetically sealing each cavity; and, forming hermetically sealed unitary suture packages from the multicavity package by cutting the package adjacent to each cavity such that each unitary package comprises a cavity bounded by gas impervious seals.

45. A method of packaging a medical device in an outer foil package, said method comprising:

providing a first substantially planar member, said member having an inner side, an outer side and an outer periphery;

locating a plurality of compartments in said first planar member, said compartments suitable for receiving a surgical suture package inserting a medical device in each compartment;

providing a second substantially planar member having an outer periphery, an outer side and a top side;

cutting a hole having an outer periphery into the second planar member, said hole centrally located therein;

mounting a gas permeable member over the opening, and sealing the member about the periphery of the opening, thereby providing a central vent;

aligning the first and second planar members such that the outer peripheries are substantially in registration;

sealing the inner sides of the planar members to form an outer gas impervious outer seal, and sides seals adjacent to each compartment, such that each compartment has an opening in communication with the central vent;

sealing off the openings in each compartment such that each compartment is bounded by gas impervious seals thereby hermetically sealing each compartment; and, forming hermetically sealed unitary suture packages from the multicompartment package by cutting the package adjacent to each compartment such that each unitary package comprises a compartment bounded by gas impervious seals.

* * * * *